(12) United States Patent
Govea

(10) Patent No.: US 9,283,378 B2
(45) Date of Patent: Mar. 15, 2016

(54) SYSTEMS AND METHODS FOR IMPLANTING AN ELECTRICAL STIMULATION LEAD USING A SHEATH

(71) Applicant: BOSTON SCIENTIFIC NEUROMODULATION CORPORATION, Valencia, CA (US)

(72) Inventor: Michael Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 274 days.

(21) Appl. No.: 13/900,247

(22) Filed: May 22, 2013

(65) Prior Publication Data

US 2013/0317518 A1   Nov. 28, 2013

Related U.S. Application Data

(60) Provisional application No. 61/651,888, filed on May 25, 2012.

(51) Int. Cl.
| | |
|---|---|
| *A61B 19/00* | (2006.01) |
| *A61N 1/05* | (2006.01) |
| *A61B 17/34* | (2006.01) |
| *A61B 17/00* | (2006.01) |

(52) U.S. Cl.
CPC .......... *A61N 1/0551* (2013.01); *A61B 17/3468* (2013.01); *A61B 2017/00331* (2013.01)

(58) Field of Classification Search
CPC ............... A61B 2017/00331; A61B 2017/003; A61B 5/04001; A61B 5/0476; A61N 1/0551; A61N 1/3605

USPC ...................... 606/129; 607/116, 117, 48, 43; 600/377, 373, 544, 545
See application file for complete search history.

(56) References Cited

U.S. PATENT DOCUMENTS

| | | | |
|---|---|---|---|
| 4,512,351 | A | 4/1985 | Pohndorf |
| 6,181,969 | B1 | 1/2001 | Gord |
| 6,516,227 | B1 | 2/2003 | Meadows et al. |

(Continued)

FOREIGN PATENT DOCUMENTS

| | | |
|---|---|---|
| WO | 2005/023359 A1 | 3/2005 |
| WO | 2010083308 A1 | 7/2010 |
| WO | 2010148380 A1 | 12/2010 |

OTHER PUBLICATIONS

International Application No. PCT/US2013/042278, International Search Report and Written Opinion mailed Aug. 19, 2013.

*Primary Examiner* — Todd E Manahan
*Assistant Examiner* — Majid Jamialahmadi
(74) *Attorney, Agent, or Firm* — Lowe Graham Jones PLLC; Bruce E. Black

(57) ABSTRACT

A method for implanting an electrical stimulation lead into a patient includes inserting an elongated sheath into a patient. The sheath includes a sheath body with a proximal end and a distal tip. The sheath defines a lumen extending from the proximal end of the sheath to the distal tip. The distal tip of the sheath is advanced to the patient's epidural space. The distal tip of the sheath is positioned at a target implantation location. A lead is advanced along the lumen of the sheath from the proximal end of the sheath body to the distal tip. The lead includes a lead body and a plurality of electrodes disposed along a distal end of the lead body. The sheath is removed from the patient while leaving the distal end of the lead at the target implantation location.

15 Claims, 13 Drawing Sheets

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2006/0089633 A1* | 4/2006 | Bleich ............... A61B 17/1659 606/32 |
| 2007/0150036 A1 | 6/2007 | Anderson |
| 2008/0188916 A1* | 8/2008 | Jones ............... A61B 17/3415 607/116 |
| 2010/0179562 A1* | 7/2010 | Linker ............... A61N 1/0551 606/129 |
| 2010/0324570 A1* | 12/2010 | Rooney ............. A61M 25/0662 606/129 |
| 2012/0022454 A1* | 1/2012 | Wall ................. A61B 17/3401 604/175 |
| 2013/0204270 A1* | 8/2013 | Howard ............. A61B 17/3439 606/129 |
| 2014/0114385 A1* | 4/2014 | Nijhuis et al. ................ 607/117 |

* cited by examiner

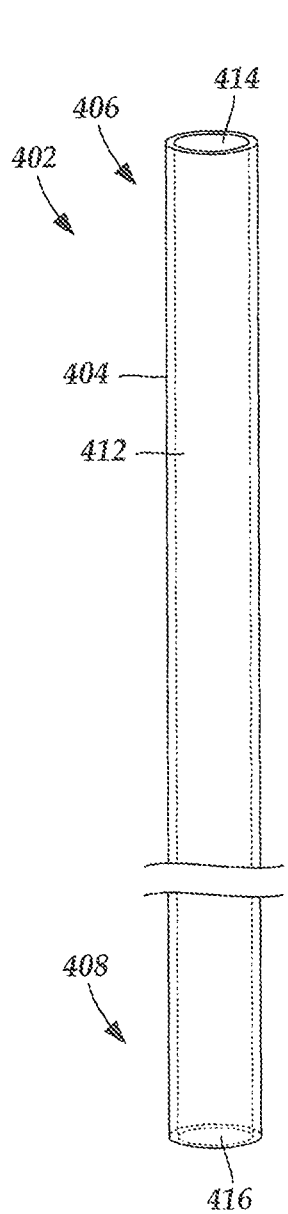
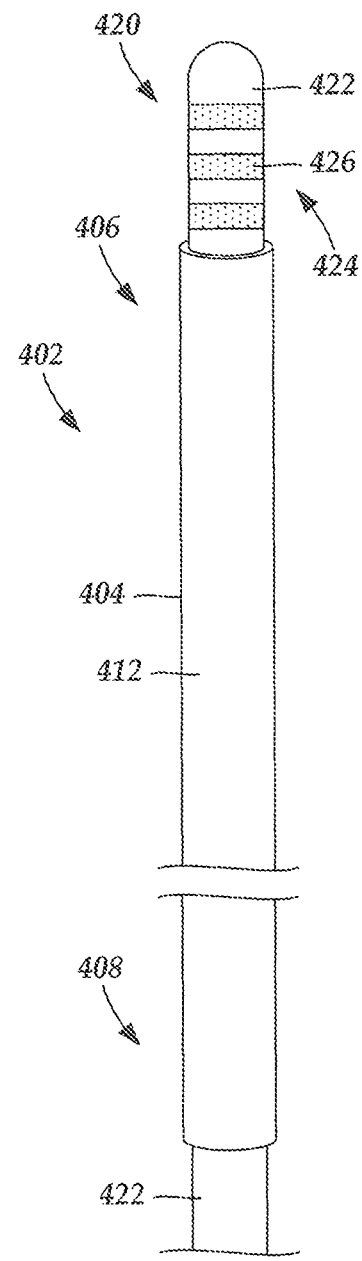
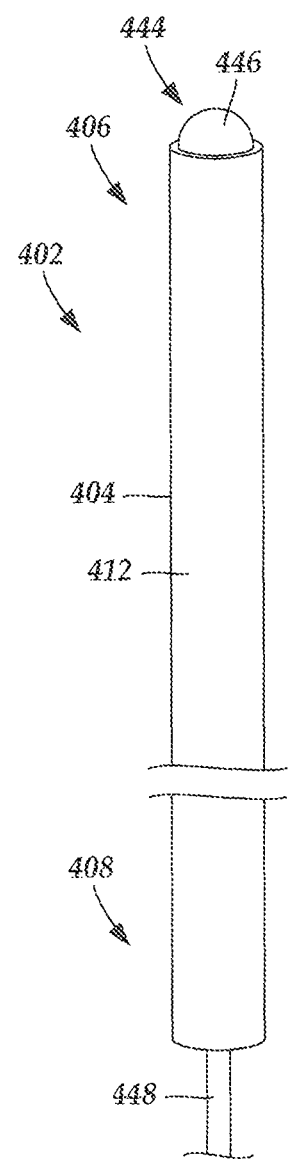
Fig. 4A
Fig. 4B
Fig. 4C

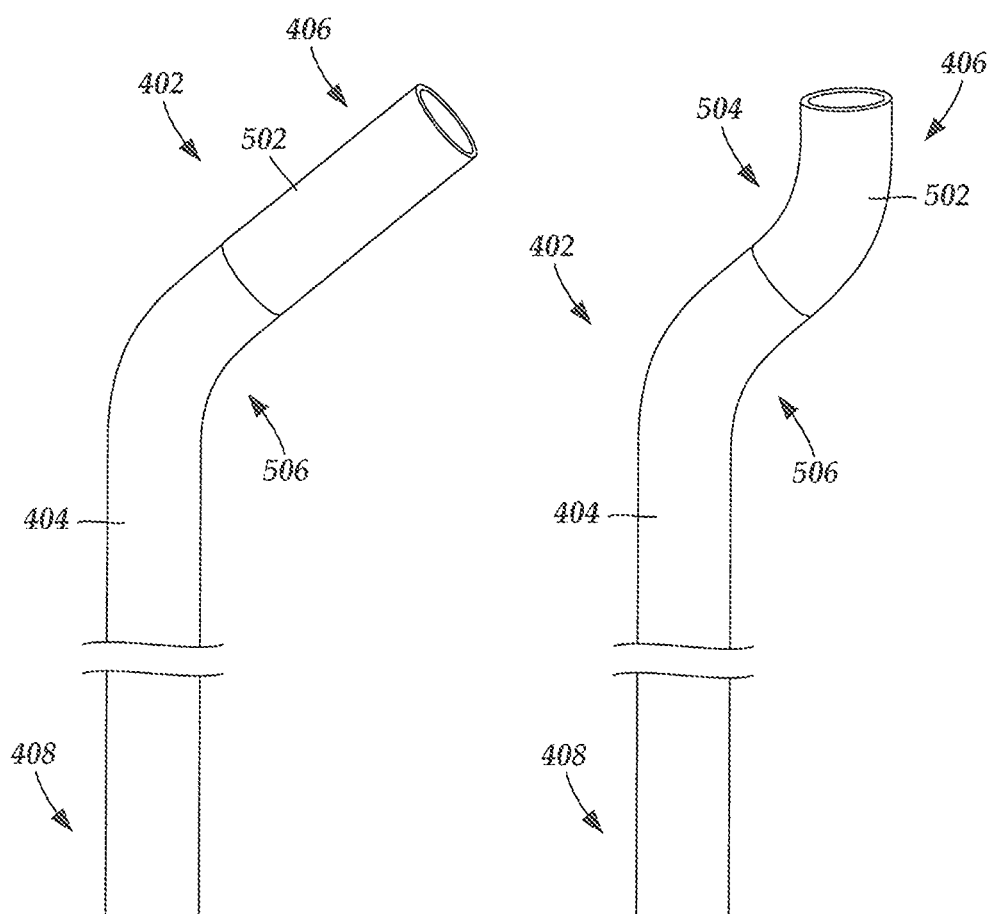

US 9,283,378 B2

SYSTEMS AND METHODS FOR IMPLANTING AN ELECTRICAL STIMULATION LEAD USING A SHEATH

CROSS-REFERENCE TO RELATED APPLICATIONS

This application claims the benefit under 35 U.S.C. §119 (e) of U.S. Provisional Patent Application Ser. No. 61/651, 888 filed on May 25, 2012, which is incorporated herein by reference.

FIELD

The present invention is directed to the area of implantable electrical stimulation systems and methods of making and using the systems. The present invention is also directed to implantation of electrical stimulation leads in proximity to a target stimulation region using a sheath, as well as methods of making and using the sheaths, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Dorsal root ganglia are nodules of cell bodies disposed along the dorsal roots of spinal nerves. Dorsal root ganglia are disposed external to the epidural space. Dorsal root ganglia, however, are disposed in proximity to the spinal cord and the vertebral column.

BRIEF SUMMARY

In one embodiment, a method for implanting an electrical stimulation lead into a patient includes inserting an elongated sheath into a patient. The sheath includes a sheath body with a proximal end and a distal tip. The sheath defines a lumen extending from the proximal end of the sheath to the distal tip. The distal tip of the sheath is advanced to the patient's epidural space. The distal tip of the sheath is positioned at a target implantation location. A lead is advanced along the lumen of the sheath from the proximal end of the sheath body to the distal tip. The lead includes a lead body and a plurality of electrodes disposed along a distal end of the lead body. The sheath is removed from the patient while leaving the distal end of the lead at the target implantation location.

In another embodiment, an insertion kit for facilitating implantation of a percutaneous lead in proximity to a dorsal root ganglion includes a percutaneous lead and an elongated sheath. The percutaneous lead includes a lead body with a proximal end, a distal end, and a longitudinal length. A plurality of electrodes is disposed along the distal end of the lead body. A plurality of terminals is disposed along the proximal end of the lead body. A plurality of conductors electrically couples the plurality of electrodes to the plurality of terminals. The elongated sheath includes a sheath body having a proximal end, a distal tip, and a longitudinal length. A distal opening is disposed at the distal tip of the sheath body. A proximal opening is disposed at the proximal end of the sheath body. A lumen extends between the distal opening and the proximal opening. The lumen forms a continuous passageway along the longitudinal length of the sheath body. The lumen is configured and arranged to receive the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of one embodiment of a sheath suitable for receiving a lead and for inserting into a patient, according to the invention;

FIG. 4B is a schematic perspective view of one embodiment of a lead extending along a lumen defined in the sheath of FIG. 4A, according to the invention;

FIG. 4C is a schematic perspective view of one embodiment of a plug inserted into a lumen of the sheath of FIG. 4A, according to the invention;

FIG. 5C is a schematic perspective view of yet another embodiment of the sheath of FIG. 4A, the sheath including a pre-defined bend and a flexible region disposed at a distal tip of the sheath, according to the invention;

FIG. 5D is a schematic perspective view of one embodiment of the sheath of FIG. 5C, the sheath bent along the flexible region of FIG. 5C, according to the invention;

DETAILED DESCRIPTION

The present invention is directed to the area of implantable electrical stimulation systems and methods of making and using the systems. The present invention is also directed to implantation of electrical stimulation leads in proximity to a target stimulation region using a sheath, as well as methods of making and using the sheaths, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
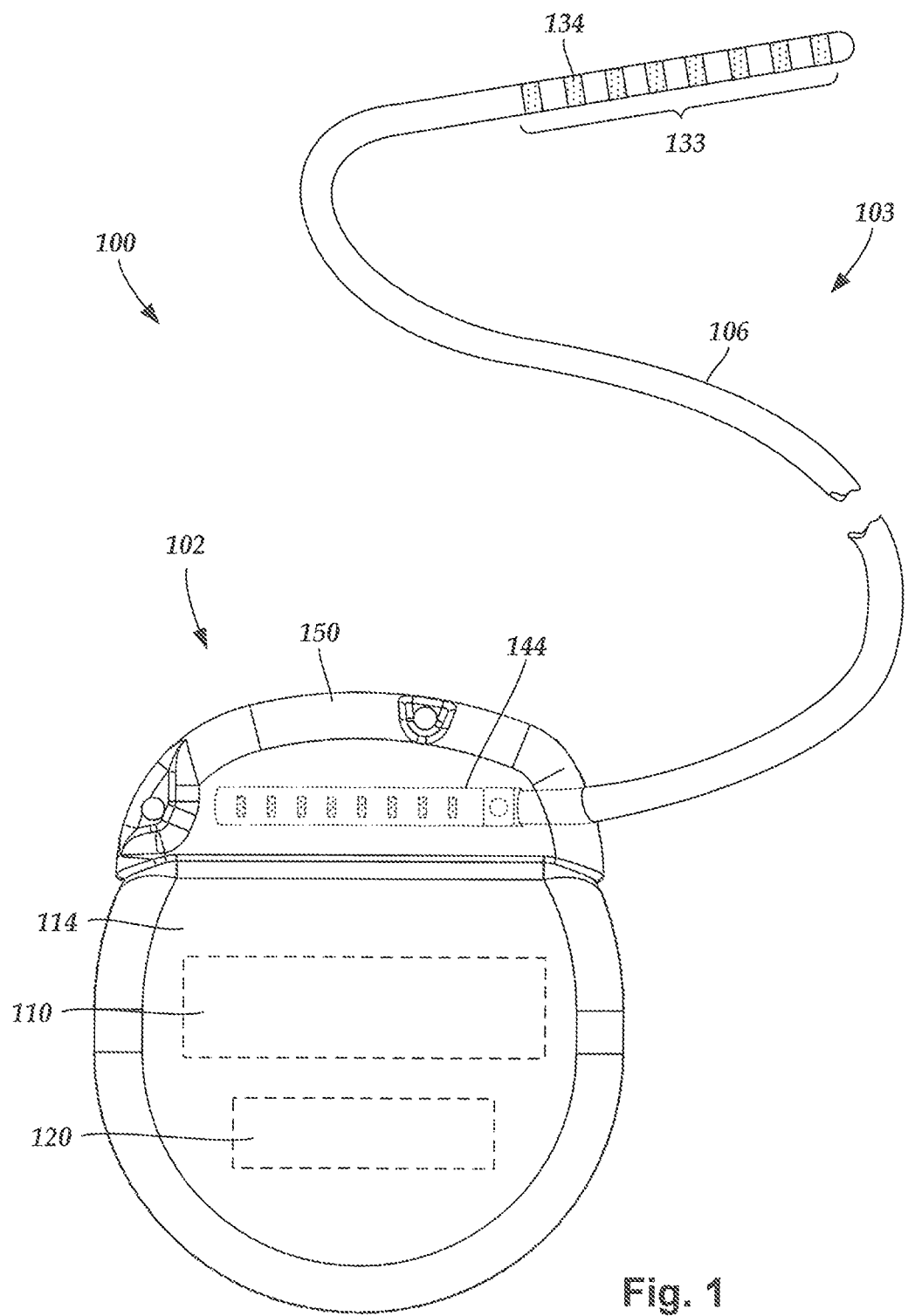
FIG. 1 is a schematic view of another embodiment of an electrical stimulation system that includes a percutaneous lead body coupled to a control module, according to the invention.

FIG. 1 illustrates schematically one embodiment of an electrical stimulation system 100. The electrical stimulation system 100 includes a control module (e.g., a stimulator or pulse generator) 102 and a percutaneous lead 103. The lead 103 includes a plurality of electrodes 134 that form an array of electrodes 133. The control module 102 typically includes an electronic subassembly 110 and an optional power source 120 disposed in a sealed housing 114. The lead 103 includes a lead body 106 coupling the control module 102 to the plurality of electrodes 134. In at least some embodiments, the lead body 106 is isodiametric.

The control module 102 typically includes one or more connector assemblies 144 into which the proximal end of the lead body 106 can be plugged to make an electrical connection via connector contacts (e.g., 216 in FIG. 2A) disposed in the connector assembly 144 and terminals (e.g., 210 in FIG. 2A) disposed along the lead body 106. The connector contacts are coupled to the electronic subassembly 110 and the terminals are coupled to the electrodes 134. Optionally, the control module 102 may include a plurality of connector assemblies 144.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 224 (see FIG. 2C) can be disposed between the lead body 106 and the control module 102 to extend the distance between the lead body 106 and the control module 102.

The electrical stimulation system or components of the electrical stimulation system, including the lead body 106 and the control module 102, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the lead body 106 are typically disposed in, or separated by, a non-conductive, biocompatible material including, for example, silicone, polyurethane, and the like or combinations thereof. The lead body 106 may be formed in the desired shape by any process including, for example, molding (including injection molding), casting, and the like. Electrodes and connecting wires can be disposed onto or within a paddle body either prior to or subsequent to a molding or casting process. The non-conductive conductive material typically extends from the distal end of the lead body 106 to the proximal end of the lead body 106.

Terminals (e.g., 210 in FIG. 2A) are typically disposed at the proximal end of the lead body 106 for connection to corresponding conductive contacts (e.g., 216 in FIG. 2A) in one or more connector assemblies (e.g., 144 in FIG. 1) disposed on, for example, the control module 102 (or to other devices, such as conductive contacts on a lead extension, an operating room cable, a splitter, an adaptor, or the like).

Conductive wires (see e.g., 508 of FIG. 5B) extend from the plurality of terminals (see e.g., 210 in FIG. 2A) to the plurality of electrodes 133. Typically, each of the plurality of terminals is electrically coupled to at least one of the plurality of electrodes 133. In some embodiments, each of the plurality of terminals is coupled to a single electrode 134 of the plurality of electrodes 133.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the lead 103. The one or more lumens may, optionally, be flushed continually, or on a regular basis, with saline, epidural fluid, or the like. The one or more lumens can be permanently or removably sealable at the distal end.

As discussed above, the lead body 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, the lead body 106 includes eight terminals that are shown coupled with eight conductive contacts disposed in the connector assembly 144.

Figure 2A:
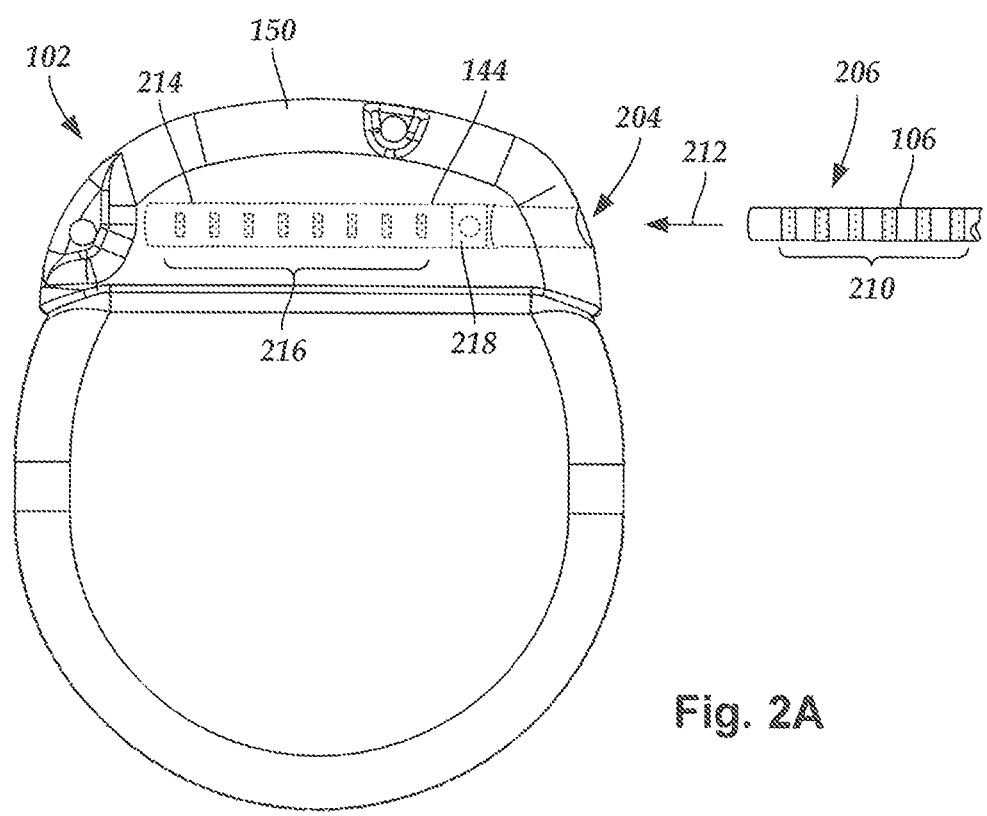
FIG. 2A is a schematic view of one embodiment of a plurality of connector assemblies disposed in the control module of FIG. 1, the connector assemblies configured and arranged to receive the proximal portions of the lead bodies of FIG. 1, according to the invention.

FIG. 2A is a schematic side view of one embodiment of a connector assembly 144 disposed on the control module 102. In FIG. 2A, the proximal end 306 of the lead body 106 is shown configured and arranged for insertion to the control module 102.

In FIG. 2A, the connector assembly 144 is disposed in the header 150. In at least some embodiments, the header 150 defines a port 204 into which the proximal end 206 of the lead body 106 with terminals 210 can be inserted, as shown by directional arrows 212, in order to gain access to the connector contacts disposed in the connector assembly 144.

The connector assembly 144 includes a connector housing 214 and a plurality of connector contacts 216 disposed therein. Typically, the connector housing 214 defines a port (not shown) that provides access to the plurality of connector contacts 216. In at least some embodiments, the connector assembly 144 further includes a retaining element 218 configured and arranged to fasten the corresponding lead body 106 to the connector assembly 144 when the lead body 106 is inserted into the connector assembly 144 to prevent undesired detachment of the lead body 106 from the connector assembly 144. For example, the retaining element 218 may include an aperture 220 through which a fastener (e.g., a set screw, pin, or the like) may be inserted and secured against an inserted lead body 106.

When the lead body 106 is inserted into the port 204, the connector contacts 216 can be aligned with the terminals 210 disposed on the lead body 106 to electrically couple the control module 102 to the electrodes (134 of FIG. 1) disposed at a distal end of the lead body 106. Examples of connector assemblies in control modules are found in, for example, U.S. Pat. Nos. 7,244,150 and 8,224,450, which are incorporated by reference.

Figure 2B:
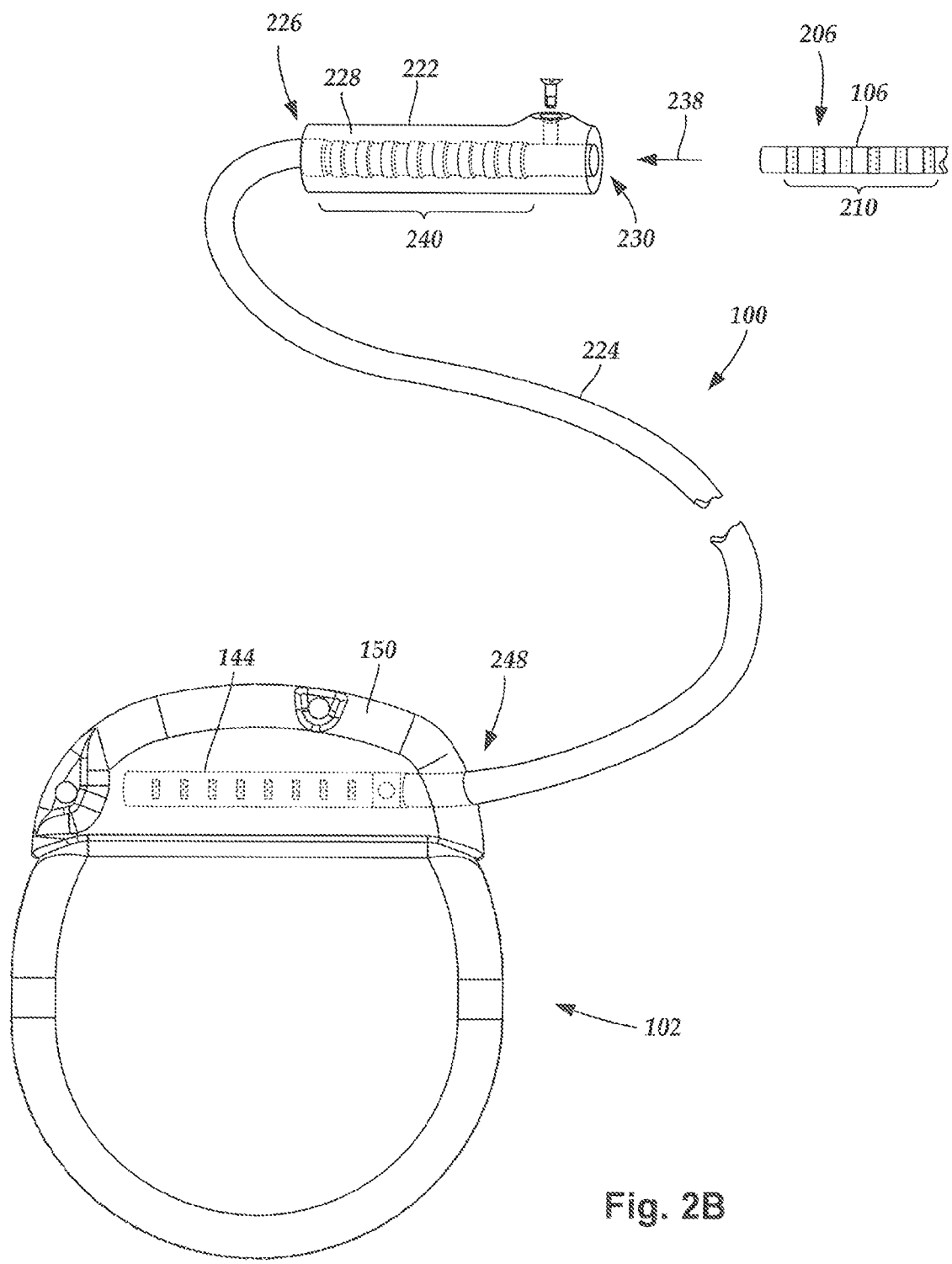
FIG. 2B is a schematic view of one embodiment of a proximal portion of the lead body of FIG. 1, a lead extension, and the control module of FIG. 1, the lead extension configured and arranged to couple the lead body to the control module, according to the invention.

In at least some embodiments, the electrical stimulation system includes one or more lead extensions. The lead body 106 can be coupled to one or more lead extensions which, in turn, are coupled to the control module 102. In FIG. 2B, a lead extension connector assembly 222 is disposed on a lead extension 224. The lead extension connector assembly 222 is shown disposed at a distal end 226 of the lead extension 224. The lead extension connector assembly 222 includes a contact housing 228. The contact housing 228 defines at least one port 230 into which a proximal end 206 of the lead body 106 with terminals 210 can be inserted, as shown by directional arrow 238. The lead extension connector assembly 222 also includes a plurality of connector contacts 240. When the lead body 106 is inserted into the port 230, the connector contacts 240 disposed in the contact housing 228 can be aligned with the terminals 210 on the lead body 106 to electrically couple the lead extension 224 to the electrodes (134 of FIG. 1) disposed at a distal end (not shown) of the lead body 106.

The proximal end of a lead extension can be similarly configured and arranged as a proximal end of a lead body. The lead extension 224 may include a plurality of conductive wires (not shown) that electrically couple the connector contacts 240 to terminal on a proximal end 248 of the lead extension 224. The conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a lead extension connector assembly disposed in another lead extension. In other embodiments (as shown in FIG. 2B), the proximal end 248 of the lead extension 224 is configured and arranged for insertion into the connector assembly 144 disposed on the control module 102.

Figure 3A:
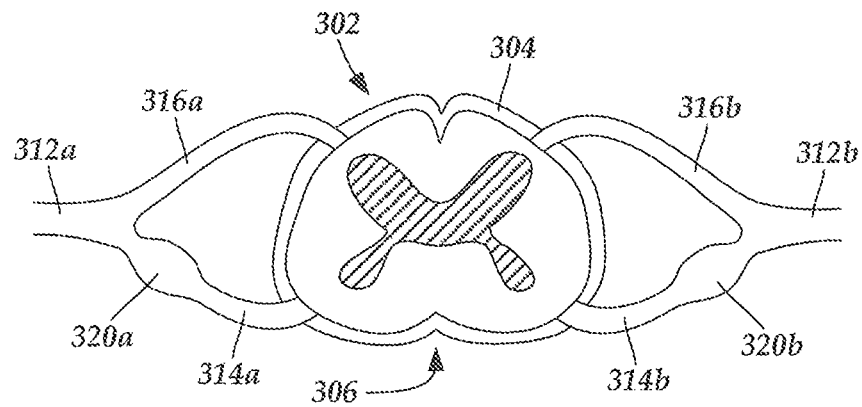
FIG. 3A is a schematic transverse cross-sectional view of spinal nerves extending from a spinal cord, the spinal nerves including dorsal root ganglia.

Turning to FIG. 3A, in at least some embodiments one or more dorsal root ganglia ("DRG") are potential target stimulation locations. FIG. 3A schematically illustrates a transverse cross-sectional view of a spinal cord 302 surrounded by dura 304. The spinal cord 302 includes a midline 306 and a plurality of levels from which spinal nerves 312*a* and 312*b* extend. In at least some spinal cord levels, the spinal nerves 312*a* and 312*b* extend bilaterally from the midline 306 of the spinal cord 302. In FIG. 3A, the spinal nerves 312*a* and 312*b* are shown attaching to the spinal cord 302 at a particular spinal cord level via corresponding dorsal roots 314*a* and 314*b* and corresponding ventral (or anterior) roots 316*a* and 316*b*. Typically, the dorsal roots 314*a* and 314*b* relay sensory information into the spinal cord 302 and the ventral roots 316*a* and 316*b* relay motor information outward from the spinal cord 302. The DRG 320*a* and 320*b* are nodules of cell bodies that are disposed along the dorsal roots 316*a* and 316*b* in proximity to the spinal cord 302.

Figure 3B:
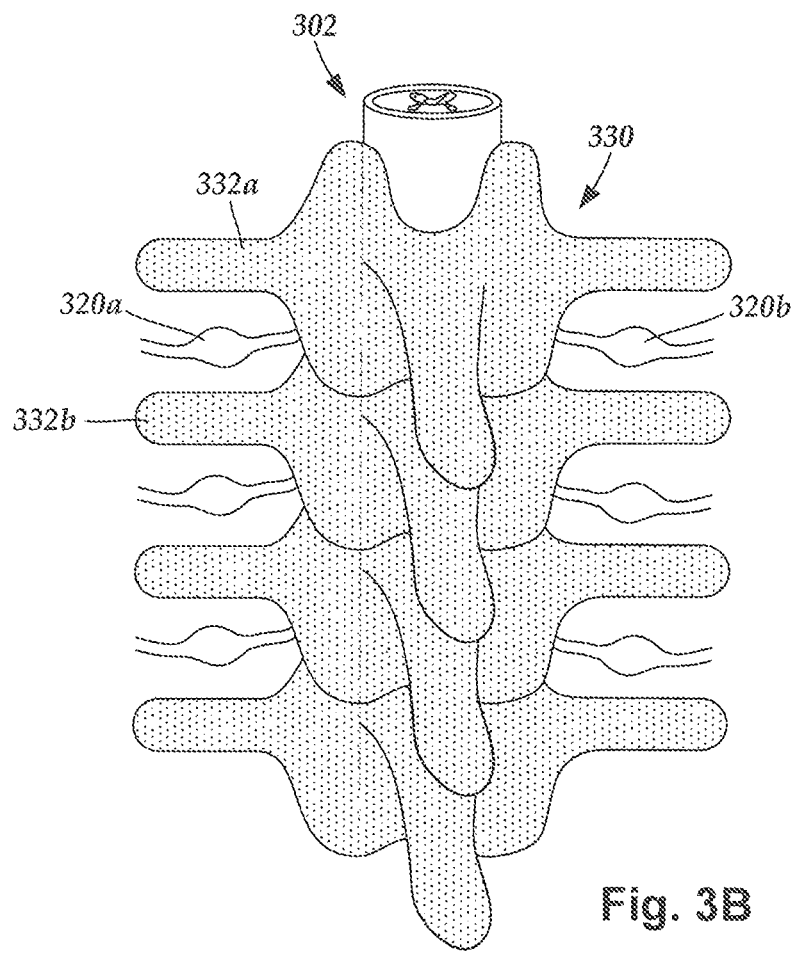
FIG. 3B is a schematic perspective view of a portion of the spinal cord of FIG. 3A disposed in a portion of a vertebral column with the dorsal root ganglia of FIG. 3A extending outward from the vertebral column.

FIG. 3B schematically illustrates a perspective view of a portion of the spinal cord 302 disposed along a portion of a vertebral column 330. The vertebral column 330 includes stacked vertebrae, such as vertebrae 332*a* and 332*b*, and a plurality of DRGs 320*a* and 320*b* extending outwardly bilaterally from the spinal cord 302 at different spinal cord levels.

Figure 3C:
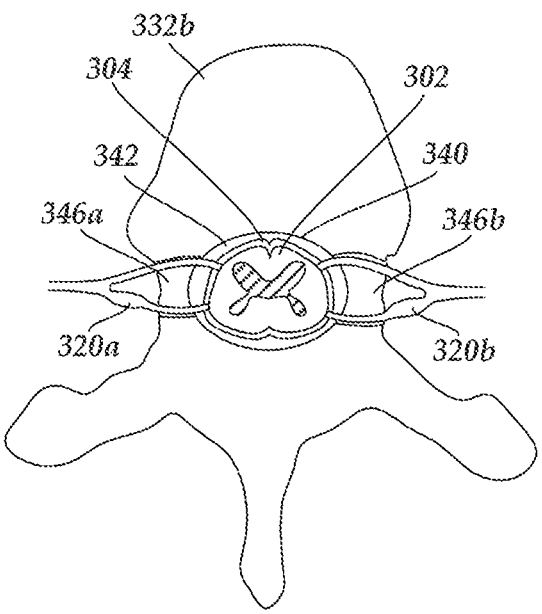
FIG. 3C is a schematic top view of a portion of the spinal cord of FIG. 3A disposed in a vertebral foramen defined in a vertebra of the vertebral column of FIG. 3B, the vertebra also defining intervertebral foramina extending between an outer surface of the vertebra and the vertebral foramen, the intervertebral foramina providing an opening through which the dorsal root ganglia of FIG. 3B can extend outward from the spinal cord of FIG. 3B.

FIG. 3C schematically illustrates a top view of a portion of the spinal cord 302 and surrounding dura 304 disposed in a vertebral foramen 340 defined in the vertebra 332*b*. The vertebrae, such as the vertebrae 332*a* and 332*b*, are stacked together and the vertebral foramina 340 of the vertebrae collectively form a spinal canal through which the spinal cord 302 extends. The space within the spinal canal between the dura 304 and the walls of the vertebral foramen 340 defines the epidural space 342. Intervertebral foramina 346*a* and 346*b*, defined bilaterally along sides of the vertebra 332*b*, form openings through the vertebra 332*b* between the epidural space 342 and the environment external to the vertebra 332*b*.

Figure 3D:
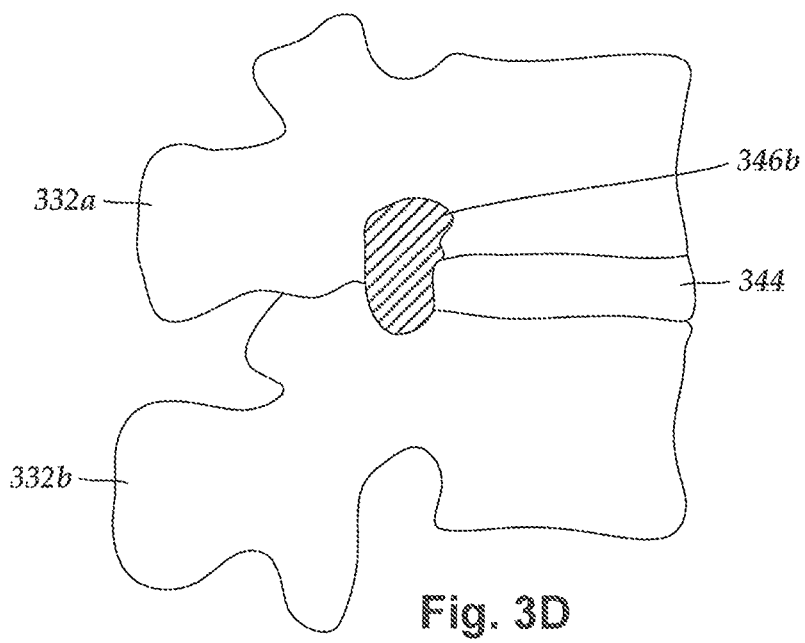
FIG. 3D is a schematic side view of two vertebrae of the vertebral column of FIG. 3B, the vertebrae defining an intervertebral foramen through which one of the dorsal root ganglia of FIG. 3B can extend outward from the spinal cord of FIG. 3B.

FIG. 3D schematically illustrates a side view of two vertebrae 332*a* and 332*b* coupled to one another by a disc 344. In FIG. 3D, the intervertebral foramen 346*b* is shown defined between the vertebrae 332*a* and 332*b*. The intervertebral foramen 346*b* provides an opening for one or more of the dorsal root 314*b*, ventral root 316*b*, and DRG 320*b* to extend outwardly from the spinal cord 302 to the environment external to the vertebrae 332*a* and 332*b*.

Turning to FIG. 4A, although the DRG are not within the epidural space, the DRG may be accessible to a lead from within the epidural space via the intervertebral foramina. In at least some embodiments, once the distal end of the lead is inserted into the epidural space the distal end of the lead can be advanced out of the epidural space through one of the intervertebral foramen, and positioned in proximity to the desired DRG.

As herein described, a sheath may be used to facilitate implantation of a lead in proximity to a DRG via the patient's epidural space. In at least some embodiments, an insertion kit for implanting a percutaneous lead into a patient includes the lead and the sheath for facilitating implantation of the lead.

FIG. 4A is a schematic perspective view of one embodiment of a sheath 402 suitable for insertion into a patient. The sheath 402 includes a sheath body 404 having a distal tip 406 and an opposing proximal end 408. The sheath 402 defines a lumen 412 extending between a distal opening 414 defined at the distal tip 406 and a proximal opening 416 defined at the proximal end 408. In at least some embodiments, the lumen 412 defines a continuous passageway extending between the distal opening 414 and the proximal opening 416.

The sheath body 404 can be rigid, flexible, or a combination thereof. The body 404 can be formed from any material (e.g., metals, alloys, composites, plastics, or the like) suitable for insertion into a patient. Optionally, the body 404 may include radiopaque material to facilitate determination of the positioning of the sheath 402, for example, when the sheath 402 is disposed in the patient through medical imaging.

Turning to FIG. 4B, the lumen 412 is configured and arranged to receive a lead. The lumen 412 can have any suitable transverse cross-sectional shape including, for example, round, oval, triangular, rectangular, or the like. In at least some embodiments, the transverse cross-sectional shape of the lumen 412 corresponds with a transverse cross-sectional shape of an outer surface of a widest portion of the lead to be inserted into the lumen 412.

FIG. 4B is a schematic perspective view of one embodiment of a portion of a lead 420 extending along the lumen 412. The lead 420 includes a lead body 422 with a distal end 424. A plurality of electrodes, such as electrode 426, is disposed along the distal end 424 of the lead body 422. In at least some embodiments, the lead 420 is a percutaneous lead (see e.g., FIG. 1). In at least some embodiments, the lead body 422 is isodiametric. In FIG. 4B, the distal end 424 of the lead 420 and at least some of the electrodes 426 are shown extending distally outward from the lumen 412.

In at least some embodiments, at least one of the plurality of electrodes 426 is configured as a ring electrode that extends completely around a radius of curvature of the lead body 422. In at least some other embodiments, at least one of the plurality of the electrodes 426 is configured such that the at least one electrode 426 extends around less than complete revolution about the lead body 422. For example, at least one of the plurality of electrodes 426 may be formed as a segmented electrode, a cuff-shaped electrode, an arc-shaped electrode, a tip electrode, or the like. It may be advantageous to form one or more of the electrodes 426 such that the one or more electrodes 426 extend around less than complete revolution about the lead body 422 so that energy propagated from the one or more electrodes 426 can be directed primarily in the direction of the target stimulation location.

As mentioned above, in at least some embodiments the sheath body 404 is rigid. As discussed in more detail below, with reference to FIGS. 6A-6B, in at least some embodiments the sheath 402 is used to form an incision in the patient extending from an external location on the patient to the patient's epidural space. In which case, it may be beneficial for the sheath body 404 to be sufficiently rigid to form the incision. In embodiments where the sheath is used to form an incision through patient tissue it may, additionally, be beneficial for the distal tip 406 of the sheath to be sufficiently sharp to pierce patient skin and to advance through patient tissue.

In at least some embodiments, it may be beneficial to insert a plug into the lumen 412 of the sheath 402 during, for example, advancement of the sheath 402 into the epidural space to reduce or prevent coring of patient tissue. FIG. 4C is a schematic perspective view of one embodiment of a plug 444 inserted into the sheath 402. In at least some embodiments, the plug 444 has a tip 446 disposed in proximity to the distal tip 406 of the sheath 402 and an elongated tail 448 that is reachable by a practitioner from the proximal end 408 of the sheath. The tip 446 can be either blunt or sharp.

In at least some embodiments, the plug 444 is formed as one of an obturator, a trocar, a stylet, or the like. In at least some embodiments, the plug 444 is also used to provide rigidity to the sheath 402 to facilitate advancement. In at least some embodiments, the plug 444 is disposed in the lumen 412 of the sheath 402 during advancement of the sheath 402 through patient tissue. In which case, the plug 444 may be removed prior to inserting the lead 420 into the lumen 412, when less rigidity is needed.

Turning to FIGS. 5A-5D, in at least some embodiments the sheath 402 is configured and arranged to be advanced to a target implantation location. The target implantation location may be the target stimulation location (e.g., the DRG), or another nearby location (e.g., the epidural space). In some instances, the target implantation location may not be conveniently accessible from an external location on the patient via a straight line. Accordingly, it may be advantageous for the sheath to include at least one bend. It may also be advantageous for the sheath to be flexible, or to include one or more flexible regions, to enable the sheath to negotiate one or more anatomical curves during advancement to the target implantation location.

Figure 5A:
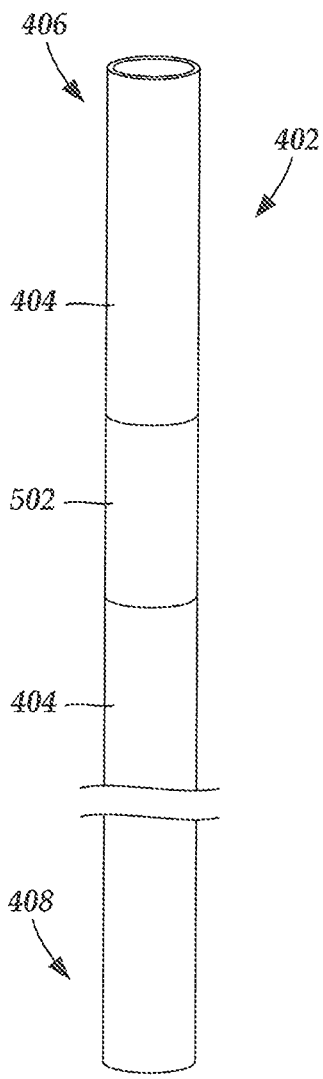
FIG. 5A is a schematic perspective view of another embodiment of the sheath of FIG. 4A, the sheath including a flexible region intermediate to a proximal end and a distal tip of the sheath, according to the invention.
Figure 5B:
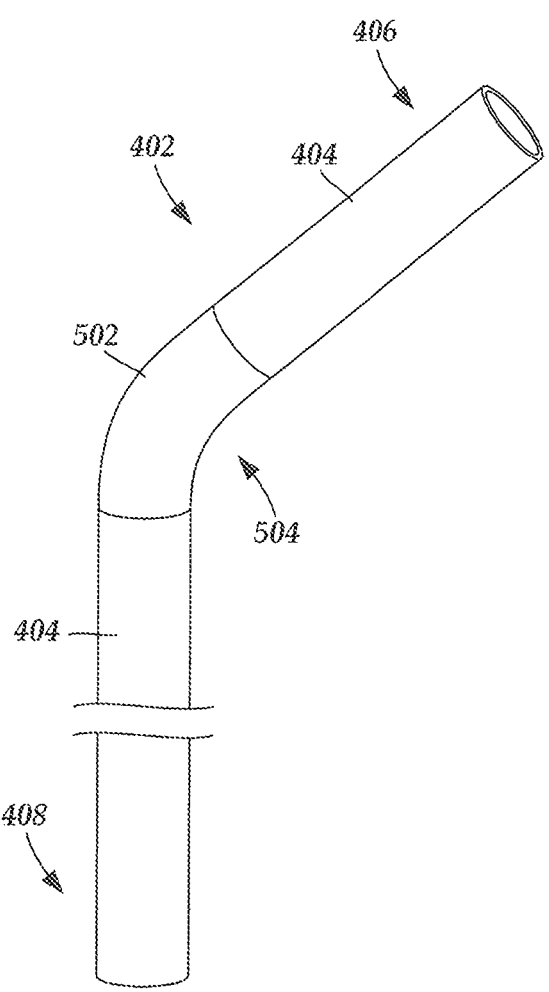
FIG. 5B is a schematic perspective view of one embodiment of the sheath of FIG. 5A, the sheath bent along the flexible of FIG. 5A, according to the invention.

FIG. 5A is a schematic perspective view of another embodiment of the sheath 402 that includes a flexible region 502 intermediate to the distal tip 406 and the proximal end 408 of the sheath 402. In FIG. 5A, the flexible region 502 is disposed in a straight configuration. FIG. 5B is a schematic perspective view of one embodiment of the sheath 402 with the flexible region 502 transitioned into a bent position such that the sheath 402 includes at least one bend 504.

It will be understood that the one or more flexible regions 502 are relatively flexible, as compared to the remaining portions of the sheath body 404. In at least some embodiments, the one or more flexible regions 502 are sufficiently flexible to enable a practitioner to bend the one or more flexible regions 502 into a desired angle immediately prior to (or during) an implantation procedure. In at least some embodiments, the one or more flexible regions 502 are sufficiently rigid enough to maintain the shape of the one or more bends 504 formed along the flexible regions 502 during the implantation procedure.

In at least some embodiments, the sheath includes one or more pre-defined bends formed along the sheath body. FIG. 5C is a schematic perspective view of yet another embodiment of the sheath 402. A pre-defined bend 506 is formed along the sheath body 404. The pre-defined bend 506 can be formed along any portion of the sheath body 404. In at least some embodiments, the pre-defined bend 506 is formed along the sheath 402 intermediate to the distal tip 406 and the proximal end 408 of the sheath 402. In at least some embodiments, a pre-defined bend is formed at the distal tip 406 of the sheath 402. It may be advantageous to form the pre-defined bend 404 at the distal tip 406, or in proximity to the distal tip 406, to facilitate advancement of the sheath 404 within the patient.

The sheath 402 can include one or more pre-defined bends 504, one or more flexible regions 502, or both. FIG. 5C shows the sheath 402 also including a flexible region 502 in addition to the pre-defined bend 504. In FIG. 5C, the flexible region 502 is disposed in a straight configuration along the distal tip 406 of the sheath body 404. FIG. 5D is a schematic perspective view of one embodiment of the sheath 402 with the flexible region 502 moved into a bent position such that the sheath 402 includes at least one bend 504.

In at least some embodiments, the sheath 402 includes exactly one flexible region 502. In at least some embodiments, the sheath 402 includes a plurality of flexible regions 502. In at least some embodiments, the one or more flexible regions 502 are configured and arranged to enable the sheath 502 to be bent to form an angle that is no less than 1°, 10°, 20°, 30°, 40°, 50°, 60°, 70°, 80°, 90°, 100°, 110°, 120°, 130°, 140°, 150°, 160°, or more. In at least some embodiments, the one or more flexible regions 502 are configured and arranged to enable the sheath 502 to be bent to form an angle that is no greater than 160°, 150°, 140°, 130°, 120°, 110°, 100°, 90°, 80°, 70°, 60°, 50°, 40°, 30°, 20°, 10°, 1°, or less.

Any suitable number of pre-defined bends can be formed along the sheath body 404. The one or more pre-defined bends 506 may be formed in addition to, or in lieu of, the one or more bends 504 that are formable along a flexible region 502 of the sheath 402. In at least some embodiments, the one or more pre-defined bends each form an angle that is no less than 1°, 10°, 20°, 30°, 40°, 50°, 60°, 70°, 80°, 90°, 100°, 110°, 120°, 130°, 140°, 150°, 160°, or more. In at least some embodiments, the one or more pre-defined bends each form an angle that is no greater than 160°, 150°, 140°, 130°, 120°, 110°, 100°, 90°, 80°, 70°, 60°, 50°, 40°, 30°, 20°, 10°, 1°, or less.

In at least some embodiments, the one or more pre-defined bends are formed during manufacture or prior to distribution to practitioners. In at least some embodiments, the one or more pre-defined bends are angled such that the pre-defined bends are configured and arranged for insertion into the epidural space from a location external to the patient. In at least some embodiments, the one or more pre-defined bends are angled such that the pre-defined bends are configured and arranged for insertion into an intervertebral foramen from inside the epidural space.

Figure 6A:
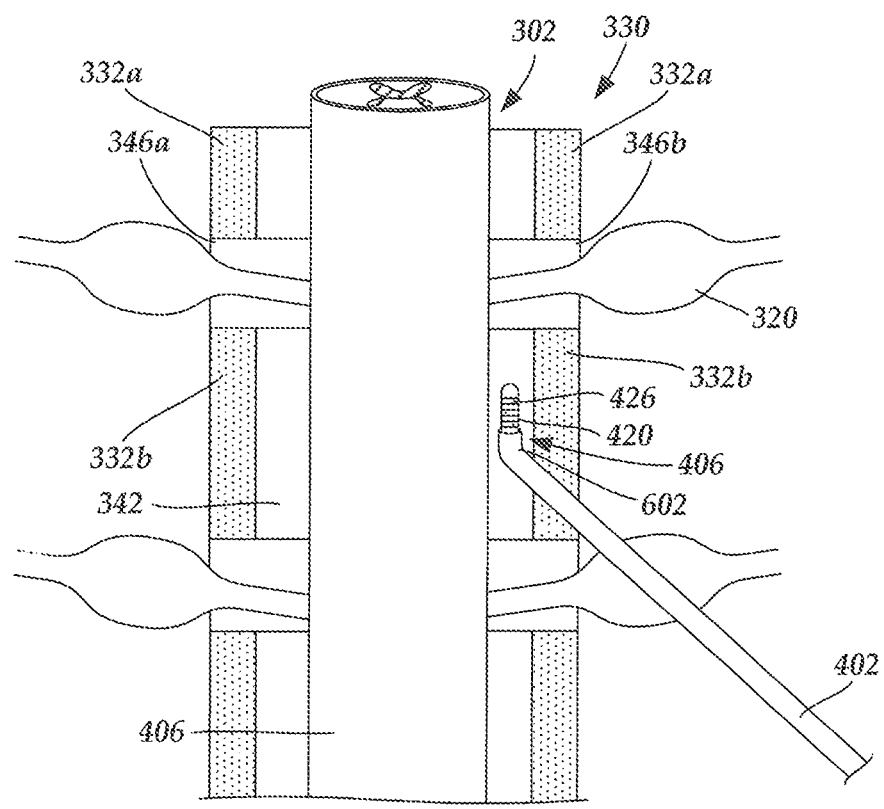
FIG. 6A is a schematic perspective view of the spinal cord of FIG. 3A disposed along a longitudinal transverse view of a portion of the vertebral column of FIG. 3B, where a perspective view of one embodiment of the distal tip of the sheath of FIG. 4A is shown inserted into an epidural space between the spinal cord and the vertebral column from a location external to the vertebral column, and where a distal end of a lead is exposed through the distal tip of the sheath, according to the invention.

Turning to FIGS. 6A-7B, in at least some embodiments the target implantation location is a location in proximity to the target stimulation location. For example, in at least some embodiments the target implantation location is the epidural space. FIG. 6A is a schematic perspective view of the spinal cord 302 disposed along a longitudinal transverse view of a portion of the vertebral column 330. The portion of the vertebral column 330 shown in FIG. 6A includes the vertebrae 332a and 332b and intervertebral foramina 346a and 346b defined between the vertebrae 332a and 332b on opposing sides of the vertebral column 330. The DRG 320 extends outward from one side of the spinal cord 302 and through the intervertebral foramen 346b.

In FIG. 6A, the distal tip 406 of the sheath 402 is shown disposed in the epidural space 342. In at least some embodiments, a bend 602 is formed along the sheath 402. The bend 602 enables the distal tip 406 of the sheath 402 to be re-oriented from its trajectory entering the epidural space 342 to correspond with the directionality of the epidural space 342. The bend 602 can be either a pre-defined bend (see e.g., bend 506) or a bend formed along a flexible region (see e.g., bend 504). In some embodiments, a single bend is formed along the sheath 402. Alternately, two or more bends may be formed along the sheath 402. In at least some embodiments, the sheath 402 is steerable to facilitate advancement of the sheath to the target implantation location. The sheath 402 can be steered in any suitable manner including, for example, using a stylet, a guidewire, or the like.

The sheath 402 can be advanced into the epidural space 342 in any suitable manner. The sheath 402 can be inserted into the epidural space 342 using a fully or partially pre-formed incision extending between the epidural space and an external location on the patient, or the sheath 402 can be used to form all, or a portion of the incision extending between the epidural space and an external location on the patient.

In at least some embodiments, the sheath 402 is advanced along the incision by itself. Optionally, the plug (444 in FIG. 4C) may be disposed in the sheath 402 during insertion into the epidural space 342 to reduce or prevent coring of patient tissue, or to provide stiffness to the sheath 402 (if needed), or both. Alternately, instead of inserting the plug into the sheath 402, in at least some embodiments a guide wire, a dilator, or the like may be inserted into the sheath 402 during at least a portion of the advancement of the sheath 402 to the target implantation location. Optionally, the sheath 402 may be inserted into a percutaneous needle and advanced at least partially through the incision while disposed in the percutaneous needle. In at least some embodiments, a dilator is used to enlarge a pre-formed incision prior to the advancement of the sheath 402 along the incision.

In at least some embodiments, instead of inserting the plug into the sheath 402 the lead 420 is disposed in the sheath 402 when the sheath 402 is advanced into the epidural space 342. In which case, the sheath 402 functions as a stiffener for the lead 420. Additionally, the sheath 402 may provide a broader working space for potential lead designs as the lead 420 may not have to satisfy as many requirements, as compared to conventional percutaneous lead implantation procedures. For example, the sheath 402 may support one or more deployable features on or in the lead 420. Moreover, for example, the sheath 402 may provide protection for one or more delicate features disposed on, or in, the lead 420.

In at least some embodiments, once the distal tip 406 of the sheath 402 is disposed at the target implantation location (e.g., the epidural space 342), the lead 420 is advanced along the lumen 412 of the sheath 402 to the distal tip 406 and the sheath 402 is removed from the patient, leaving the distal end of the lead 420 disposed in the epidural space 342. In at least some embodiments, the lead 420 is sufficiently stiff to be advanced along the sheath 402 without providing a stiffener. In other embodiments, the lead 420 is advanced along the sheath 402 with the aid of one or more stiffeners, such as a guidewire, a stylet, or the like.

Figure 6B:
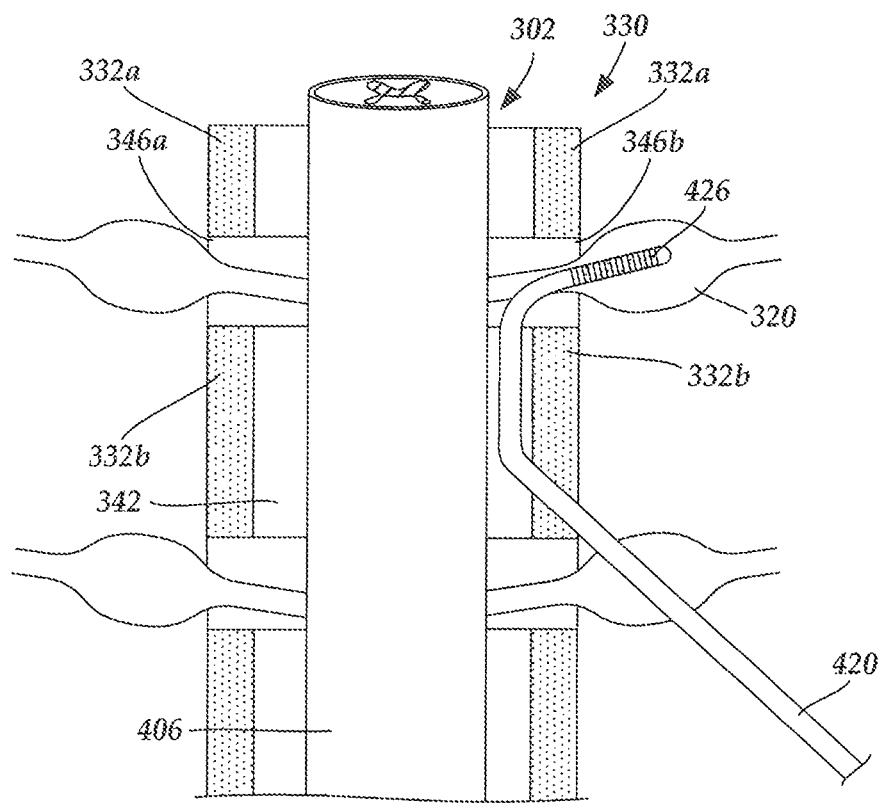
FIG. 6B is a schematic perspective view of the spinal cord of FIG. 3A disposed along a longitudinal transverse view of a portion of the vertebral column of FIG. 3B, where a perspective view of one embodiment of the distal end of the lead of FIG. 6A is shown inserted into the epidural space of FIG. 6A, extended through an intervertebral foramen, and positioned in proximity to a dorsal root ganglion, according to the invention.

In at least some embodiments, once the distal end of the lead 420 is disposed at the target implantation location (e.g., the epidural space 342) and the sheath 402 is removed, the lead 420 is advanced to the target stimulation location without the sheath 402. FIG. 6B illustrates the distal end of the lead 420 positioned near the DRG 320 such that the electrodes 426 of the lead 420 are in operational proximity to the DRG 320. When, as shown in FIG. 6B, the target stimulation location is the DRG 320, the lead 420 can be advanced out of the epidural space 342, via the intervertebral foramen 346b. The lead 420 can be guided in any suitable manner including, for example, using a stylet, a guidewire, or the like.

Figure 7A:
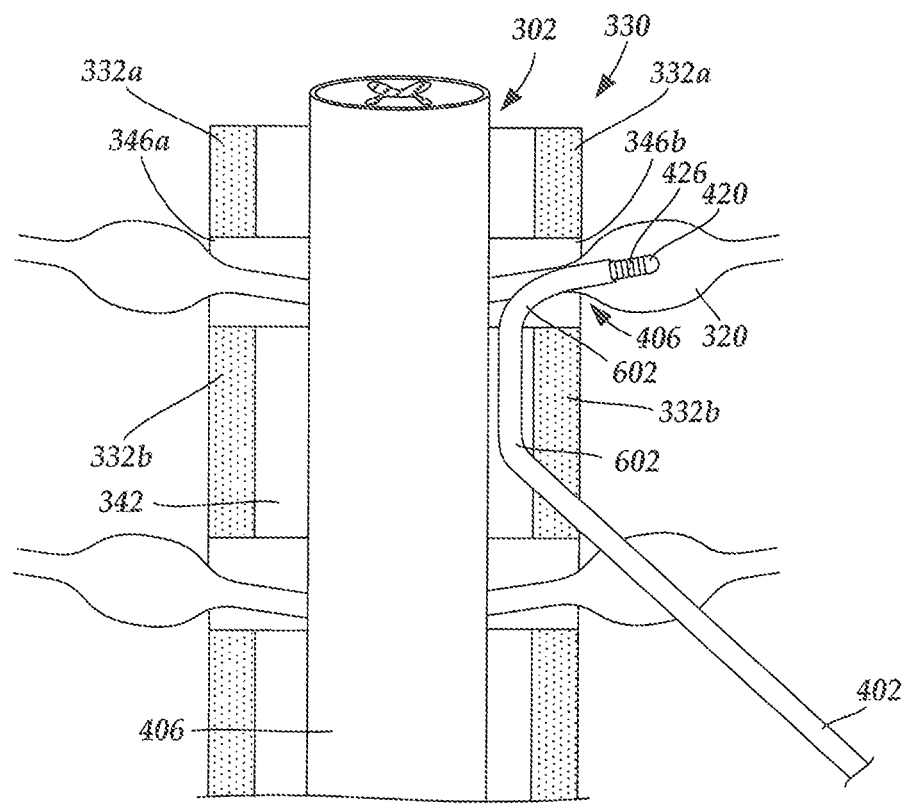
FIG. 7A is a schematic perspective view of the spinal cord of FIG. 3A disposed along a longitudinal transverse view of a portion of the vertebral column of FIG. 3B, where a perspective view of one embodiment of the distal tip of the sheath of FIG. 4A is shown inserted into the epidural space of FIG. 6A, extended through an intervertebral foramen, and positioned in proximity to a dorsal root ganglion, according to the invention.

In at least some embodiments, the target implantation location for the sheath is the target stimulation location (e.g., the DRG). FIG. 7A is a schematic perspective view of the sheath 402 inserted into the epidural space 342 and the distal tip 406 of the sheath 402 advanced out through the intervertebral foramen 346b and positioned in proximity to the DRG 320. In at least some embodiments, the sheath 402 is steerable to facilitate advancement of the sheath to the target implantation location. The sheath 402 can be steered in any suitable manner including, for example, using a stylet, a guidewire, or the like.

The sheath 402 may include any suitable number of bends 602 for facilitating advancement of the sheath 402 to the target implantation location. In FIG. 6B, the sheath 402 is shown with two bends 602. In at least some embodiments, one or more of the bends are used to temporarily anchor the sheath 402 to the vertebral column 330 until the lead 420 is advanced to the target stimulation location.

Figure 7B:
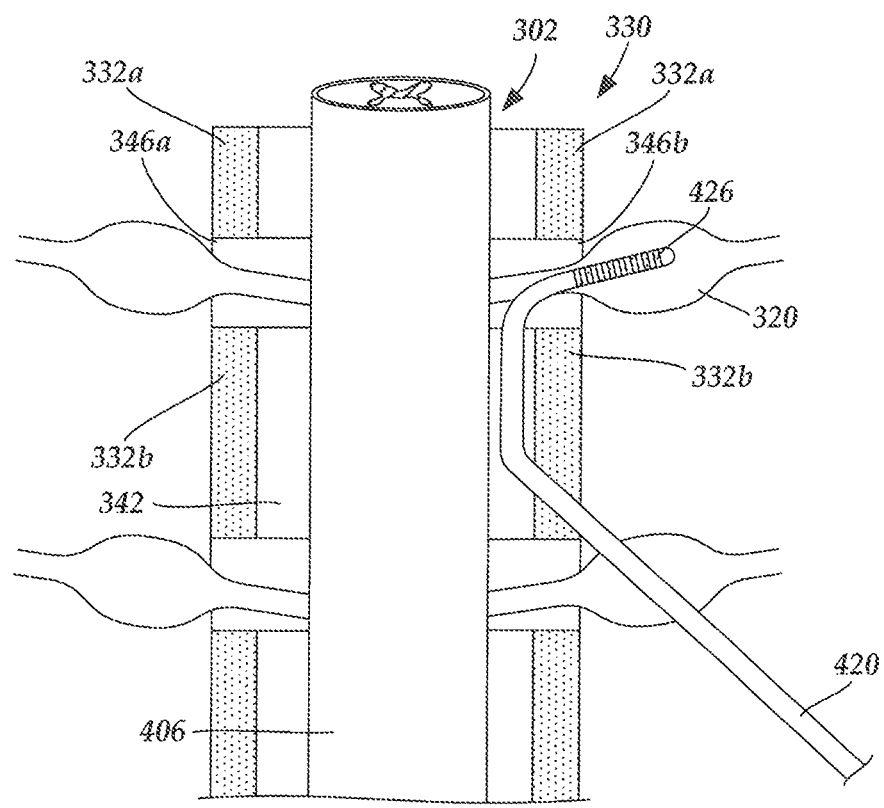
FIG. 7B is a schematic perspective view of the spinal cord of FIG. 3A disposed along a longitudinal transverse view of a portion of the vertebral column of FIG. 3B, where a perspective view of one embodiment of the distal end of the lead of FIG. 6A is shown inserted into the epidural space of FIG. 6A, extended through the intervertebral foramen of FIG. 7A, and positioned in proximity to the dorsal root ganglion of FIG. 7A, according to the invention.

Once the distal tip of the sheath 402 is positioned, the lead 420 is advanced along the sheath 402 to the distal tip 406 and the sheath 402 is removed from the patient. FIG. 7B illustrates the distal end of the lead 420 positioned near the DRG 320 such that the electrodes 426 of the lead 420 are in operational proximity to the DRG 320. As mentioned above, in at least some embodiments the lead 420 is sufficiently stiff to be advanced along the sheath 402 without providing a stiffener. In other embodiments, the lead 420 is advanced along the sheath 402 with the aid of a guidewire, stylet, or the like.

It may be advantageous to advance the sheath 402 to the target stimulation location. When the sheath 402 is advanced all the way to the target stimulation location, the lead 420 can be positioned at the target stimulation location without needing to separately advance the sheath 402 part of the way to the target stimulation location, and then advance the lead 420 the rest of the way to the target stimulation location. Additionally, advancing the lead 420 all of the way to the target stimulation location from within the sheath 402 enables the lead 420 to be formed all, or in part, from a flexible (e.g., floppy) material that may otherwise be difficult to advance to the target stimulation location using conventional techniques.

Figure 8:
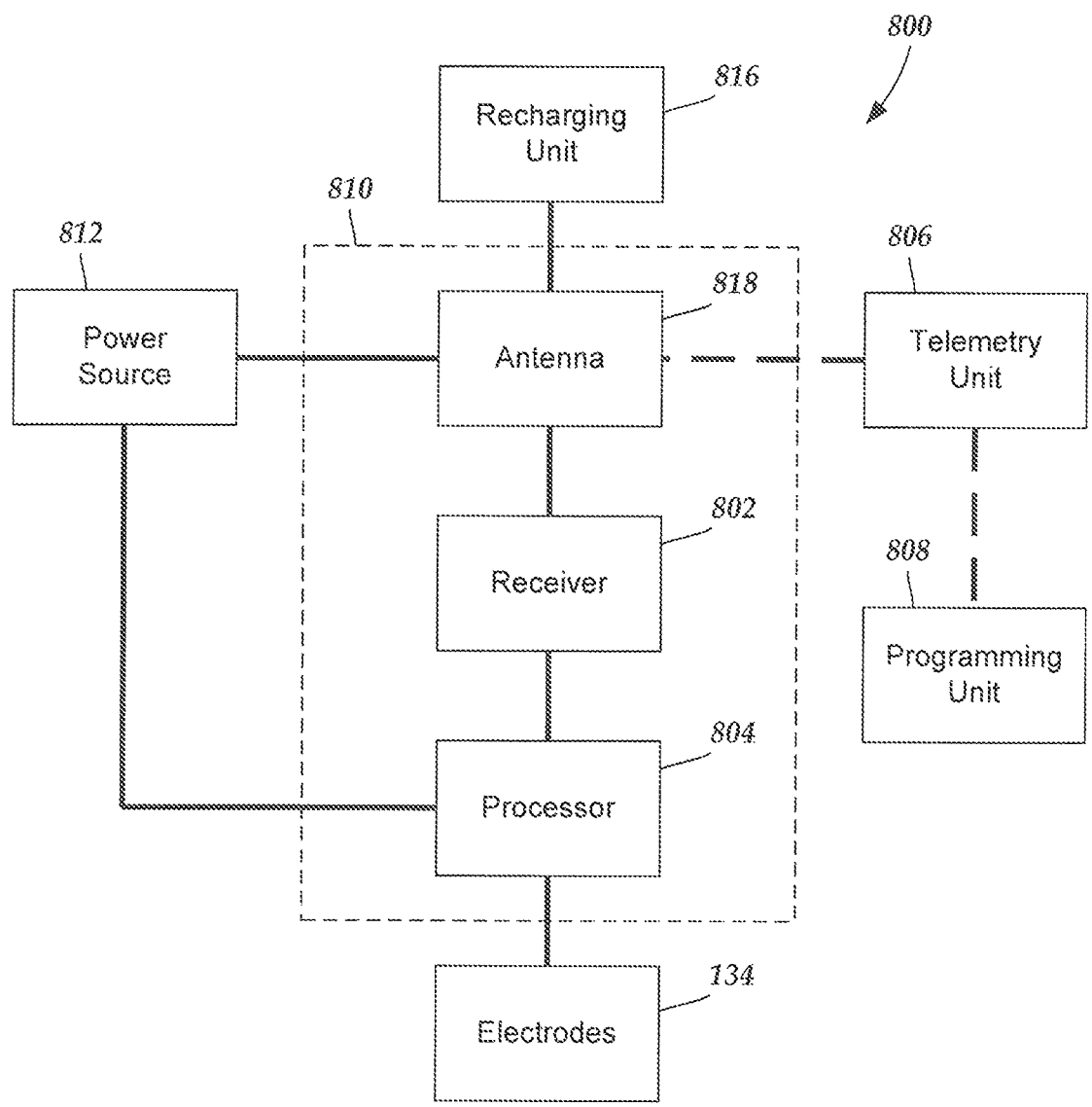
FIG. 8 is a schematic overview of one embodiment of components of an electrical stimulation system, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for implanting an electrical stimulation lead into a patient, the method comprising:
    inserting an elongated sheath into a patient, the sheath comprising a sheath body with a proximal end and a distal tip, the sheath defining a lumen extending from the proximal end to the distal tip;
    advancing the distal tip of the sheath to the patient's epidural space;
    guiding the distal tip of the sheath into and through an intervertebral foramen from a location inside the epidural space;
    positioning the distal tip of the sheath at a target implantation location;
    advancing a lead along the lumen of the sheath from the proximal end of the sheath body to the distal tip, the lead comprising a lead body and a plurality of electrodes disposed along a distal end of the lead body; and
    removing the sheath from the patient while leaving the distal end of the lead at the target implantation location.

2. The method of claim 1, wherein advancing the distal tip of the sheath to the patient's epidural space comprises using the distal tip of the sheath to form an incision extending between an exterior location of the patient and the patient's epidural space.

3. The method of claim 2, further comprising inserting a plug into the sheath prior to using the distal tip of the sheath to form the incision extending between the exterior location of the patient and the patient's epidural space.

4. The method of claim 1, wherein advancing the distal tip of the sheath to the patient's epidural space comprises inserting the sheath into a percutaneous needle and using the percutaneous needle to form an incision extending between an exterior location of the patient and the patient's epidural space.

5. The method of claim 1, wherein advancing the distal tip of the sheath to the patient's epidural space comprises extending the sheath through a previously-formed incision extending between an exterior location of the patient and the patient's epidural space.

6. The method of claim 5, further comprising enlarging the previously-formed incision with a dilator prior to extending the sheath through the previously-formed incision.

7. The method of claim 1, wherein positioning the distal tip of the sheath at a target implantation location comprises steering the sheath using one of a stylet or a guidewire.

8. The method of claim 1, further comprising guiding the distal end of the lead from the target implantation location to a target stimulation location.

9. The method of claim 8, wherein guiding the distal end of the lead from the target implantation location to the target stimulation location comprises inserting one of a stylet or a guidewire into the lead body to facilitate guidance of the lead.

10. The method of claim 1, wherein positioning the distal tip of the sheath at a target implantation location comprises guiding the distal tip of the sheath to a target stimulation location.

11. The method of claim 1, further comprising bending, the sheath along at least one flexible region of the sheath body prior to guiding the distal tip of the sheath into and through the intervertebral foramen from inside the epidural space and aligning the bent at least one flexible region with an interface between the epidural space and the intervertebral foramen.

12. The method of claim 1, wherein guiding the distal tip of the sheath into and through an intervertebral foramen from a location inside the epidural space comprises aligning at least one pre-defined bend formed along the sheath with an interface between the epidural space and the intervertebral foramen.

13. The method of claim 1, wherein positioning the distal tip of the sheath at a target implantation location further comprises positioning the distal end of the lead in proximity to a dorsal root ganglion that extends through the intervertebral foramen.

14. The method of claim 1, wherein advancing the lead along the lumen of the sheath comprises inserting one of a stylet or a guidewire into the lead body to facilitate advancement of the lead.

15. The method of claim 1, further comprising disposing a radiopaque material along at least a portion of the sheath body prior to inserting the sheath into a patient.

* * * * *